United States Patent

Barcelo et al.

[11] Patent Number: 4,652,665
[45] Date of Patent: Mar. 24, 1987

[54] α-CHLORINATED CARBONATES

[75] Inventors: Gérard Barcelo, Ste Genevieve des Bois; Jean-Pierre Senet, La Chapelle la Reine; Gérard Sennyey, Gif sur Yvette, all of France

[73] Assignee: Societe Nationale des Poudres et Explosifs, Paris, France

[21] Appl. No.: 701,429

[22] Filed: Feb. 14, 1985

[30] Foreign Application Priority Data

Feb. 16, 1984 [FR] France ................. 84 02328

[51] Int. Cl.$^4$ ............ C07C 69/96; C07C 68/02
[52] U.S. Cl. .................... 556/437; 558/260; 558/272; 558/277
[58] Field of Search ............. 260/463; 556/437; 558/260, 277, 272

[56] References Cited

U.S. PATENT DOCUMENTS

| 3,467,690 | 9/1969 | Chamberlin | 260/463 |
| 3,875,207 | 4/1975 | Iselin et al. | 260/463 |
| 3,944,590 | 3/1976 | Iselin et al. | 260/463 |
| 4,440,692 | 4/1984 | Kalbacher et al. | 260/463 |

FOREIGN PATENT DOCUMENTS 0040153 11/1981 European Pat. Off.
828871 2/1960 United Kingdom.

OTHER PUBLICATIONS

Hales et al., *Chemical Abstracts*, vol. 51: 7148f, 1957.

*Primary Examiner*—Donald G. Daus
*Assistant Examiner*—Stephen Kapner
*Attorney, Agent, or Firm*—Bucknam and Archer

[57] ABSTRACT

The invention relates to new α-chlorinated carbonates characterized in that their formula is:

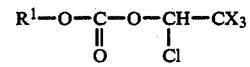

in which X is a fluorine, chlorine or bromine atom and $R^1$ is different from the

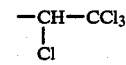

group and represents;

a substituted or non-substituted, saturated or unsaturated, aliphatic, araliphatic, primary, secondary, tertiary or cycloaliphatic radical.

These α-chlorinated carbonates are prepared by the action of a compound of formula $R^1OH$ on a chloroformate of formula:

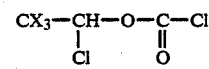

in a solvent medium in the presence of an acid scavenger which is added after the two preceding compounds.

They are used to block the amine function of amino acids. The α-chlorinated carbonate and amino acid are reacted in a solvent medium at a temperature of −5° to 100° C. in the presence of an acid scavenger. Blocked amines are very useful in peptide synthesis.

1 Claim, No Drawings

α-CHLORINATED CARBONATES

The invention relates to new α-chlorinated carbonates, their method of manufacture and application in the protection of the amine functions of amino acids.

Carbonates are compounds in great demand which are used in a large variety of fields such as solventss, plasticisers, lubricants, transesterification agents or intermediates in the production of peptides.

To perform syntheses in which amino acids are involved, the amine function of these acids must be protectd temporarily. This amine function is very often blocked by conversion into a carbamate function which prevents recemization when coupling and is readily cleaved, for example, by acidolysis, hydrogenolysis, or any other known method (E. Schroeder and K. Lubke, ("The Peptides", Vol. 1, page 39, Academic Press, New York and London,, 1965).

The most commonly used groups for that purpose are:
benzyloxy carbonyl (Z),
tertiary butyloxycarbonyl (BOC),
fluorenylmethyloxy carbonyl (FMOC),
trichloroethyloxycarbonyl (TROC),
vinyloxycarbonyl (VOC).

The tertiary butyloxycarbonyl (B0C) group is particularly in demand.

These protecting groups are generally introduced by the action of the corresponding chloroformate on the amine function.

However, chloroformates cannot always be used. Some are not very stable or else they are difficult to manipulate. This is the case, for example, of p-methoxybenzyl, furfuryl or tertiary-butyl chloroformates. The last of these, for example, even when prepared in situ is not satisfactory because of the formation ofureas in the presence of excess phosgene.

Other carbamation agents have been suggested such as:
azides of various protecting groups. Their synthesis is achieved in several stages and is difficult. They can decompose explosively, like the azide of BOC:
fluroides of BOC, p-methoxybenzyl or furfuryl, but their preparation is difficult because this requires the use of commercially not available raw materials such as CLCOF or BrCOF, which must be manipulated with caution;
some tests have been performed with very particular carbonates, such as mixed carbonates of protecting groups and p-nitrophenyl but they do not react with all amino acids. An alcohol or a phenol is formed, which is often difficult to eliminate and the reaction is reversible;
dicarbonates of protecting groups. Their synthesis is difficult and costly. In addition, a protecting radical is lost;
carbonates of oxime, hydroxysuccinimide, enol or S-dimethyl-pyrimidyl, which also are difficult to prepare and require costly raw materials.

There has therefore existed for many years now an unsatisfied need for some new compounds that are easy to make with good yields and are stable compounds that can be used without difficulty to attach the most important protecting groups onto the amine function of amino acids and do not have the disadvantages of the previously mentioned compounds.

According to the invention the new α-chlorinated carbonates have the general formula:

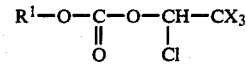

in which X is a fluorine, chlorine or bromine atom and $R^1$ is different from

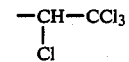

and represents:
a substituted or non-substituted, saturated or unsaturated, aliphatic, araliphatic, primary, secondary, tertiary or cycloaliphatic radical.

In preference, X is a chlorine atom and $R^1$ a saturated or unsaturated, substituted or non-substituted $C_1$ to $C_{20}$ aliphatic or $C_7$ to $C_{20}$ araliphatic radical. The substituents of $R^1$ can be very varied. They are, for example, halogen atoms, groups including silicon, heterocyclic or non-heterocyclic groups including nitrogen, oxygen or sulfur atoms.

In particular, $R^1$ is chosen from groups normally used to protect the amine functions of amino acids in the form of carbamates, such as tertiary butyl, paranitrobenzyl, 9-fluorenylmethyl, 2,2,2,-trichloroethyl, trimethylsilylethyl.

According to the invention, the new α-chlorinated carbonates are prepared by reacting the hydroxylated compound of formula $R^1OH$ with an α-chlorinated chloroformate of formula:

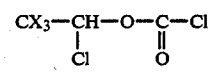

X and $R^1$ having the same meaning as before, in a solvent medium at a temperature of $-20°$ to $-50°$ C. in the presence of a hydrochloric acid scavenger which is added after the two reagents.

The following reaction takes place:

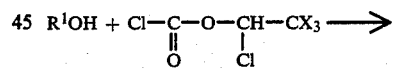

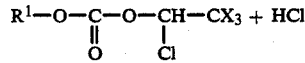

The solvent medium consists of one or several solvents inert to the reagents. Chlorinated aliphatic solvents, for example, dichloromethane or dichloroethane, cyclic or acyclic ethers, ketones, such as acetone or 2-butanone, nitriles, esters or aliphatic or aromatic hydrocarbons are chosen preferentially.

The acid scavenger is generally an organic base or inorganic base. Pyridine or triethylamine are used preferentially.

The base is added after the two reagent compounds, preferably gradually.

The temperature is preferentially between $-5°$ and $+5°$ C. On completion of the reaction the temperature of the mixture can be raised to the ambient temperature for a few minutes to several hours.

The α-chlorinated chloroformates themselves can be prepared by chlorination of chloroformates or preferably by phosgenation of the corresponding aldehydes as described in European Patent Application No. 40153.

The starting compounds and the base are generally introduced in stoichiometric quantity. An excess of alcohol can be used. The carbonate obtained is easily isolated by the usual methods.

The carbonates of the invention have never until now been described in the literature. The presence of a

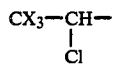

group in their structure gives them great originality and very specific properties which make them very useful as intermediates in synthesis.

The invention relates in particular to an application of the new α-chlorinated carbonates.

In this application, the previously described α-chlorinated carbonates are used to protect the amine function of amino acids.

More precisely they are reacted in a solvent medium in the presence of a hydrochloric acid scavenger at a temperature between −5° and 100° C. with an amino and/or imino carboxylic acid including at least one hydrogen atom on the amino or imino group of formula

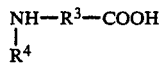

in which $R^3$ and $R^4$ independently or jointly are the usual radicals of amino acids.

The reaction can be represented by:

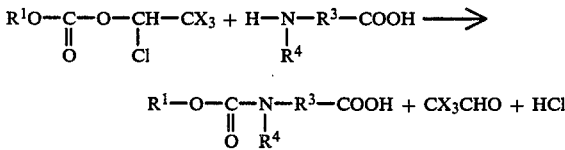

This reaction is surprising as there is an elimination of HCl but not with attachment of the amino group to the carbon atom to which the chlorine is attached:

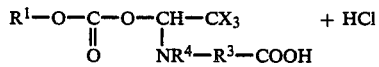

as could normally be expected and as is the case for example when an α-chlorinated compound reacts with an acid:

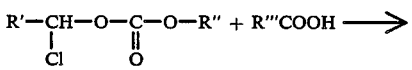

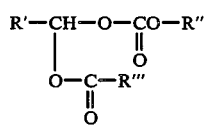

(ASTRA—FR Patent No. 2 201 870)

On the contrary, the new α-chlorinated compounds cleave, the radical,

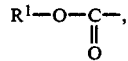

which attaches itself to the nitrogen atom of the amino acid and an aldehyde, $CX_3CHO$, is formed.

As starting amino acids or imino carboxylic acids can be used natural or synthetic, optically active or inactive, or racemic compounds still containing one hydrogen atom fixed onto the amino or imino group.

The radical $R^3$ or $R^4$ can contain blocked or non-blocked functional groups such as amino, imino, mercapto, hydroxyl or carboxyl. The radical $R^4$ is generally a hydrogen atom and $R^3$ is a substituted or non-substituted, saturated or unsaturated $C_1$ to $C_{20}$ aliphatic radical or a substituted or non-substituted, saturated or unsaturated $C_7$ to $C_{20}$ araliphatic radical.

The heterocycle formed by $R^3$ and $R^4$ and the nitrogen atom can have 4 to 6 members; it can be saturated or unsaturated, substituted or non-substituted, condensed or not condensed to other rings, for example, aromatic rings.

The acid can be in the form of one of its derivatives, for example, an ester or an amide.

The invention usually applies to alpha amino acids but beta, gamma and delta amino acids can also be used.

The carboxylic group can also be replaced by a sulfonic or phosphoric group.

By way of examples of amino acids can be cited L-phenylalanine, L-proline, glycine, L-tyrosine, L-serine, L-aspartic acid, ethyl glycinate, phenylglycine, L-alanine.

As α-chlorinated carbonates are used preferentially those in which X is a chlorine atom and the radical $R^1$ one of the most commonly used protecting groups to acylate the amine function, for example, 1,2,2,2 tetrachloro ethyl and 2′,2′,2′ trichloroethyl, 9-fluorenylmethyl, paranitrobenzyl or 2-trimethylsilylethyl carbonates. These carbonates are in particular greatly favoured in the case of unprotected hydroxyamino acids, such as L-serine or L-tyrosine. The 1,2,2,2 tetrachloroethyl and tertiary butyl carbonate is particularly interesting.

The presence of an acid scavenger is necesary to eliminate the hydrochloric acid which is formed during the reaction. This can be effected by means or an organic or inorganic base.

Among the prefered bases are sodium or potassium hydroxide, sodium or potassium carbonate or bicarbonate, or magnesium oxide, which are generally used in the form of an aqueous solution, or tertiary amines, for example, pyridine and triethylamine.

The basic substance is usually added in excess, preferably about 1.1 to 3 equivalents per amine function to be protected.

It can be advantageous to maintain the pH constant throughout the reaction by means of standard apparatus.

The solvent medium can consist of one or several solvents that are inert to the reagents. As preferred organic solvent are chosen preferentially chlorinated aliphatic solvents such as dichloromethane, 1,2 dichloroethane, cyclic or acyclic ethers, for example, tetrahydrofuran or dioxan, acetone, pyridine, acetonitrile, dimethylformamide, alcohols such as ethanol or tertiary butanol. Water can also be used alone or mixed with the above solvents. A 1:1 dioxan/water mixture is particularly favoured.

The reaction temperature depends on the nature of the solvent, the reactivity of the starting compounds, as well as the other reaction conditions. It is preferentially between 0° C. and 30° C.

Atmospheric pressure is the most commonly used pressure. The reaction time is variable. It is generally between 0.5 and 36 hours, usually between 2 and 6 hours.

The starting compounds can be added in stoichiometric quantity. The use of one of the reagents in excess is preferred.

The order in which the reagents are introduced is not a fundamental characteristic of the invention. Generally the α-chlorinated carbonate is added after the amino acid.

The blocked amino acids can be recovered easily and isolated in crystallized form if necessary by converting them into an ammonium salt, for example, a dicyclohexylammonium salt.

Using the new α-chlorinated carbonates of the invention obtained from available raw materials and a simple method according to this invention, the amino function of very varied amino acids can be blocked in the form of carbamates by means of all the known protecting groups. This was impossible or very difficult to achieve until now. The yields are very high. The reaction conditions are mild and no racemization occurs.

With the amino acids protected in this way any desired coupling operations with the acid function, as in conventional peptide synthesis, can be carried out (cf. for example, E. Gross and J. Meinhofer Ed. "The Peptides: Analysis—Synthesis—Biology", Academic Press, New York and London, Vol. 3, 1980).

These amino acid derivatives are very much used as intermediates in the manufacture of food and pharmaceutical products. The synthesis of ASPARTAM can be cited as an example (cf. Tetrahedron, Vol. 39, No. 24, pp. 4121 to 4126, 1983, B. YDE, et al.

The invention is illustrated by the following examples.

EXAMPLE 1

Synthesis of 1,2,2,2 tetrachloroethyl and tertiary-butyl carbonate 9.9 g (0.04 mole) of 1,2,2,2 tetrachloroethyl chloroformate are added at one time to a solution of tertiary butanol (3 g; 0.04 mole) in dichloromethane (50 ml). After cooling to 0° C., 3.2 g (0.04 mole) of pyridine are added drop by drop. The mixture is stirred for four hours at ambient temperature. 20 ml of chilled water are then added, the organic phase is separated and washed with 20 ml of chilled water, followed by drying over magnesium sulfate and evaporating the solvent. 11.3 g of a white solid (yield: 99%) are obtained. This is recrystallized from petroleum-ether (yield 87%; m.p.: 70° C.) and 9.9 g of pure carbonate obtained. b.p.: 96° C./866 Pa (6.5 mm Hg)

IR VCO=1770 cm$^{-1}$

NMR H$^1$(CDCL$_3$, TMS): 1.5 (s, CH$_3$) 6,7 (s, CH)

EXAMPLE 2 a. Preparation of tertiary-butyloxycarbonyl-L-phenylalanine

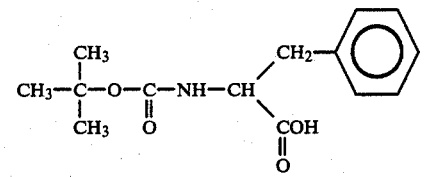

To a solution of L-phenylalanine (1.65 g; 10 mmoles) in aqueous dioxan (1:1; 30 ml) are added 4.2 ml (30 mmoles) of triethylamine and the mixture stirred until dissolution is complete (about 10 min). 2.85 g (10 mmoles) of tertiary butyl and 1,2,2,2 tetrachloroethyl carbonate are then added and the mixture stirred for six hours at 20° C. 50 ml of water are then added and extracted with 2×2 ml of ethyl acetate. The aqueous phase is acidified (pH 2-3) with N HCL and then extracted with 3×30 ml of ethyl acetate. The extract is washed with a saturated NaCl solution, dried over MgSO$_4$ and evaporated. The product obtained is crystallized from ethyl acetate and petroleum-ether. 2.1 g of the desired carbamate are obtained (yield 79%). m.p.: 85°-87° C.; m.p.$_{Lit}$=86°-88° C., optical rotation $[\alpha]_D^{20}$=+28 (c 1.5 EtOH; $[\alpha]_D^{20}{}_{Lit}$=+24.7 (c 1.5 EtOH).

b. Preparation of N-tertiarybutyloxycarbonyl-L-alanine

The procedure followed is the same as that in Example 2a.

From 1.78 g (20 mmoles) of alanine are obtained 3.4 g of BOC-L-alanine (yield: 90%).

m.p.=80°-81° C.; m.p.$_{Lit}$=83°-84° C.

$[\alpha]_D^{20}$=−24.9 (c 2.1 AcOH); $[\alpha]_D^{20}$=−22.4 (c 2.1 AcOH)

EXAMPLE 3

Preparation of tertiary-butyloxycarbonyl-L-proline

The procedure followed is the same as that in Example 2. From 1.15 g (10 mmoles) of L-proline are obtained 1.95 g of the desired carbamate (yield 91%).

m.p.=130°-131° C.; m.p.$_{Lit}$=132°-133° C.

$[\alpha]_D^{20}$=−60 (c 2.0 AcOH); $[\alpha]_D^{20}{}_{Lit}$=−60.2 (c 2.0 AcOH).

EXAMPLE 4

Preparation of tertiary-butyloxycarbonyl-glycine (BOC-Gly)

The procedure followed is the same as that in Example 2. From 0.75 g (10 mmoles) of glycine are obtained 1.5 g of the desired carbamate (yield 86%).

m.p.=80°-85° C.; m.p.$_{Lit}$=86°-88° C.

EXAMPLE 5 a. Preparation of BOC-Gly at controlled pH 5.6 g (0.075 mole) of glycine are dissolved in 150 ml of aqueous dioxan (50%) and the pH adjusted with 4N caustic soda. 23.6 g (0.083 mole) of 1,2,2,2 tetrachloroethyl and tertiary butyl carbonate are added at one time and the pH maintained constant by addition of 4N caustic soda. When the reaction is over about 200 ml of water are added and the aqueous phase then washed two times with 100 ml of ethyl-ether. The aqueous phase is then acidified to a pH of 3 with 6N HCl and extracted three times with 200 ml ethyl acetate (AcOEt). After drying and evaporation of solvent, the product is crystallized from Ac-OEt/petroleum-ether (40°-70° C.). BOC-glycine which melts at 85°-87° is obtained.

| pH | Time | Caustic soda added | Yield isolated |
|---|---|---|---|
| 10 | 5 h | 2 eq | 45% |
| 9 | 20 h | 2 eq | 71.4% |
| 8 | 30 h | 1 eq | 31% | b. The procedure followed is the same as that in (a) using various amino acids.

The results are given in the following table:

| Amino acid | pH | Yield % | m.p. °C. | $[\alpha]_D^{20}$ | c/solvent |
|---|---|---|---|---|---|
| Pro | 8.6 | 80 | 135-136 | -60 | 2/AcOH |
| Trp | 8.3 | 74 | 135-140 | -21.2 | 1/AcOH |
| Asp (OBzl) | * | 42 | 98-100 | -19 | 2/DMF |
| His (Tos) | 10 | 50 | 154 | +25.4 | 1/MeOH |
| Ala | 10.1 | 70 | 84 | -25.5 | 2/AcOH |
| Val | 9.5 | 80 | 78 | -6.0 | 1/AcOH |
| Ile | 9.5 | 71 | 66 | +3.3 | 1/AcOH |
| Leu | 9.75 | 95 | 75 | -27 | 1/AcOH |
| Met | 9.7 | 75 | oil | — | — |
| Glu(OBzl) | 9 | 42 | 132 (DCHA salt) | +13.6 | 1.1/MeOH |
| His (Tos) | * | 50 | 154 | +25.4 | 1/MeOH |
| Tyr(Bzl) | 9.8 | 43 | 98-100 | +27.4 | 2/EtOH |
| Ser (Bzl) | 9.5 | 74 | 61 | +21 | 2/EtOH 80% |
| Thr(Bzl) | 9.0 | 76 | 114 | +16.3 | 1/MeOH |
| Arg(NO₂) | 9.5 | 25 | 100-114 | -23.0 | 1.9/pyridine |
| Cys(Acm) | 9.5 | 46 | — | — | — |
| Lys(Z) | 10.2 | 84 | oil | — | — |

*based used : triethylamine

EXAMPLE 6

Preparation of tertiary-butyloxycarbonyl-L-tyrosine 1.81 g (10 mmoles) of tyrosine are dissolved in 20 ml of aqueous dioxan (1:1) by adding 1.4 ml (10 mmoles) of triethylamine and 15 mmoles of caustic soda. 2.85 g (10 mmoles) of tertiary butyl and 1,2,2,2 tetrachloroethyl carbonate are then added and the mixture stirred for six hours at 20° C. The procedure followed is the same as that in Example 2. The product obtained is crystallized as the dicyclohexyl ammonium salt. 3.8 g are obtained (yield 82%).

m.p.=206° C.; m.p.$_{Lit}$=212° C.

EXAMPLE 7

Preparation of tertiary-butyloxycarbonyl-L-serine

The procedure followed is the same as that in Example 2, but the reaction time is 24 hours instead of 6 hours. From 1.05 g (10 mmoles) of L-serine are obtained 3.1 g of the desired carbamate as the dicyclohexyl ammonium salt (yield 78%).

m.p.=139°-140° C.; m.p.$_{Lit}$=140°-142° C.

$[\alpha]_D^{20}$=+8 (C 2.8 MeOH); $[\alpha]_D^{20}{}_{Lit}$32 +13 (c=MeOH).

EXAMPLE 8

Preparation of tertiary-butyloxycarbonyl-L-aspartic acid

The procedure followed is the same as that in the preceding example.

From 1.33 g (10 mmoles) of L-aspartic acid, 1.4 g of the desired acid is obtained (yield 60%).

m.p.=116°-118° C.; m.p.$_{Lit}$=114°-116° C.

$[\alpha]_D^{20}$=-5 (c 1.0 MeOH); $[\alpha]_D^{20}{}_{Lit}$=-6.2 (c 1.0 MeOH).

EXAMPLE 9

Preparation of 1,2,2,2 tetrachloroethyl and 9-fluorenylmethyl carbonate

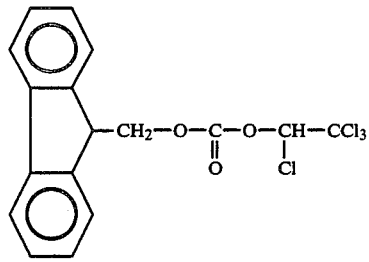

6.7 g (0.027 mole) of 1,2,2,2 tetrachloroethyl chloroformate are added at one time to a solution of 9-fluorenylmethanol (4.9 g; 0.025 mole) in 50 ml dichloromethane. The mixture is cooled to 0° C. and 2.2 ml of pyridine are added drop by drop. The mixture is stirred for four hours at 0° C. 50 ml of dichloromethane are then added and the organic phase washed twice with 50 ml of chilled water. Drying takes place over magnesium sulfate and the solvent is evaporated. The residue is crystallized from hexane and 9.3 g of the desired carbonate obtained (yield 98%).

m.p.=98°-100° C.

IR: VC=0 1750 cm⁻¹

NMR H¹: (CDCl₃, TMS) 4.5 ppm CH₂—O; 6.75 ppm

EXAMPLE 10

Preparation of 9-fluorenylmethyloxycarbonyl-L-phenylalanine

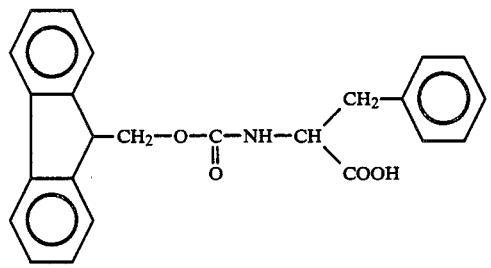

0.83 g of L-phenylalanine (5 mmoles) are dissolved in aqueous dioxan (1: 2, 12 ml) containing 1.4 ml of triethylamine (10 mmoles). The mixture is cooled to 0° C. and 2.05 g (5 mmoles) of the preceding carbonate dissolved in 4 ml of dioxan added at one time. After two hours at 0° C., 20 ml of water are added, followed by extraction twice with 20 ml of ether. The aqueous phase is then acidified (pH 2-3) with 6N HCl followed by extraction three times with 50 ml of ethyl acetate. This is followed by drying over MgSO₄ and evaporation. The product obtained crystallizes from ethyl acetate and petroleum-ether, and 1.44 g of the desired derivative obtained (yield 75%).

m.p.=178°-179° C.

m.p.$_{Lit}$=178°–179° C. (Lit: L Lapasantis et al., Synthesis (1983) 671).

EXAMPLE 11

Preparation of 9-fluorenylmethoxycarbonyl (L)-Proline (FMOC-Pro)

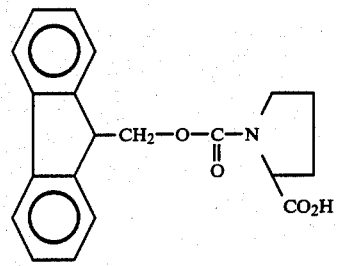

The procedure followed is the same as that in Example 10. From 0.58 g (5 mmoles) of L-Proline are obtained 1.4 g of FMOC-L-Proline (yield 83%).
m.p.=112°–113° C.; m.p.$_{Lit}$=116°–117° C.

EXAMPLE 12

Preparation of 9-fluorenylmethyloxycarbonyl-L-serine

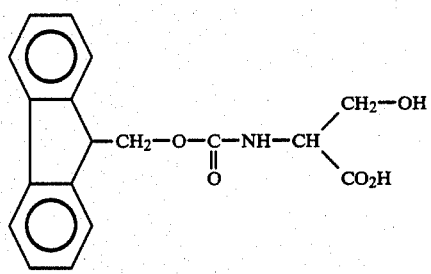

The procedure followed is the same as that in Example 10, but the reaction is continued for 24 h at 20° C. From 0.53 g (5 mmoles) of L-serine are obtained 1.32 g of FMOC-(L)-serine (yield 81%). m.p.=73°–75° C.

After recrystallization the m.p.=83°–86° C.; m.p.$_{Lit}$=86°–88° C.

EXAMPLE 13

Preparation of 2,2,2 trichloroethyl and 1',2',2',2' tetrachloroethyl carbonate

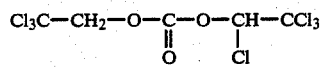

The procedure followed is the same as that in Example 1. From 14.9 g of trichloroethanol (0.1 mole) are obtained 24.1 g of the desired carbonate (yield 67%).
b.p.=108° C./6.6 Pa; m.p.=36° C.
IR VCO=1770 cm$^{-1}$
NMR H$^1$ (CDCl$_3$, TMS): 4.85 (s, CH$_2$) 6.7 (s, CH).

EXAMPLE 14

Preparation of trichloroethoxycarbonyl-L-phenylalanine-TROC-L-Phe)

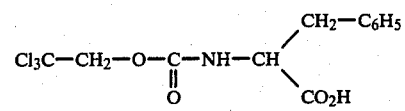

The procedure followed is the same as that in Example 10. From 0.83 g (5.5 mmoles) of L-phenylalanine and 1.98 g (5.5 mmoles) of 2,2,2 trichloroethyl and 1',2',2',2' tetrachloroethyl carbonate are obtained 1.43 g of TROC-L-phenylalanine (yield 84%).
m.p.=128°–129° C.; m.p.$_{Lit}$=129°–130° C.

EXAMPLE 15

Preparation of trichloroethyloxycarbonyl-(L)-serine

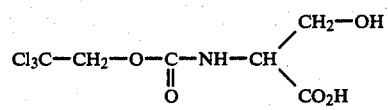

The procedure followed is the same as that in Example 12. From 0.53 g (5 mmoles) of L-serine and 1.98 g (5.5 mmoles) of carbonate of Example 13 are obtained 1.15 g of TROC-L-Serine (yield 82%).
m.p.=111°–113° C.; m.p.$_{Lit}$=114°–115° C.

EXAMPLE 16

Preparation of 1,2,2,2 tetrachloroethyl and 2-trimethylsilylethyl carbonate

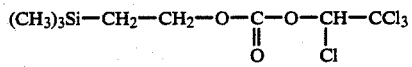

The procedurre followed is the same as that in Example 1. From 5.91 g of trimethylsilylethanol and 12.35 g of tetrachloroethyl choroformate are obtained 13.6 g of the desired product (yield 83%).
b.p.=92°–94° C./6.6 Pa.
IR VCO=1750 cm$^{-1}$
NMR H$^1$ (CDCl$_3$, TMS external)=0.1 (s, CH$_3$—Si) 1.1 (t, CH$_2$—Si) 4.35 (t, CH$_2$—O) 6.7 (s, CH—Cl)

EXAMPLE 17

Preparation of trimethylsilylethyloxycarbonyl-(L)-phenylalanine

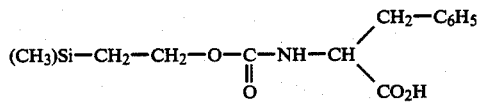

The procedure followed is the same as that in Example 12. From 0.83 g (5 mmoles) of phenylalanine and 1.8 g (5.5 mmoles) of the preceding carbonate are obtained 1.4 g of trimethylsilylethoxycarbonyl-L-phenylalanine as an oil (yield 100%).
NMR H$^1$ (CDCl$_3$, TMS) 0 (s, CH$_3$—Si) 0.9 (t, CH$_2$—Si) 3.0 (CH$_2$Ph) 4.0 (t, O—CH$_2$—C—Si) 4.5

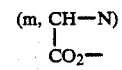

5.2 (s, NH) 7.2 (s, Ph—H)

8.7 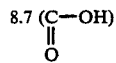

2 ml of dicyclohexylamine are added to this oil dissolved in 5 ml of ether and after crystallization 1.93 g of the dicyclohexylammonium salt obtained (yield 78%).
m.p.=111°-112° C.

EXAMPLE 18

Synthesis of p-nitrobenzyl and 1,2,2,2-tetrachloroethyl carbonate 3.83 g (25 mmoles) of p-nitrobenzyl alcohol and 6.17 g (25 mmoles) of 1,2,2,2-tetrachloroethyl chloroformate are dissolved in 50 ml of dichloromethane. After cooling to 0° C., 2.02 ml of pyridine are added drop by drop. The mixture is stirred for four hours at 10° C. and 50 ml of chilled water then added. The organic phase is separated, followed by further washing twice with 50 ml of water. The organic phase is dried over magnesium sulfate and the solvent evaporated. 8.7 g of the desired product are obtained (yield 96%).
b.p.=190°-195° C./0.5 mm Hg.
m.p.=53°-55° C. (Crystallization solvent: aqueous ethanol); crystallization yield: 54%).

We claim:
1. An α-chlorinated carbonate of formula

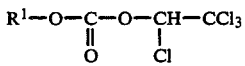

wherein $R^1$ is different from

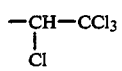

group and is tertiary butyl, para-nitrobenzyl, 9-fluorenylmethyl, 2,2,2-trichloroethyl or trimethylsilylethyl.

* * * * *